United States Patent [19]

Meguro et al.

[11] Patent Number: 4,602,027

[45] Date of Patent: Jul. 22, 1986

[54] OXAZOLEACETIC ACID DERIVATIVES

[75] Inventors: Kanji Meguro; Takeshi Fujita, both of Hyogo, Japan

[73] Assignee: Takeda Chemical Industries, Ltd., Osaka, Japan

[21] Appl. No.: 501,012

[22] Filed: Jun. 6, 1983

[30] Foreign Application Priority Data

Jun. 15, 1982 [JP] Japan .................. 57-103544

[51] Int. Cl.$^4$ ................. C07D 263/30; A61K 31/42
[52] U.S. Cl. ..................... 514/374; 548/236
[58] Field of Search ........... 548/236; 424/272; 544/236; 514/374

[56]     References Cited
    U.S. PATENT DOCUMENTS

| 3,574,228 | 4/1971 | Brown | 548/236 |
| 3,578,671 | 5/1971 | Brown | 548/236 |
| 3,579,529 | 5/1971 | Brown | 548/235 |
| 4,012,412 | 3/1977 | Yamanaka et al. | 424/272 |

FOREIGN PATENT DOCUMENTS 1695289  4/1971  Fed. Rep. of Germany ...... 548/236

OTHER PUBLICATIONS

Matsumoto, K., Patent Abst. of Japan, 1, (34) (1983) (JP-A-188587).

Primary Examiner—George F. Lesmes
Assistant Examiner—S. A. Gibson
Attorney, Agent, or Firm—Stiefel, Gross, Kurland & Pavane

[57]             ABSTRACT

A compound of the formula:

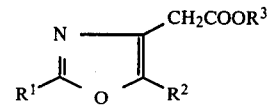

wherein $R^1$ is (A) a group of the formula,

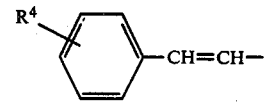

wherein $R^4$ is H, a halogen or trifluoromethyl group, or (B) a group of the formula,

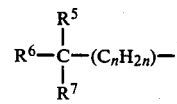

wherein n is 0 or an integer of 1 to 3; $R^5$ is H or an alkyl group of 1 to 6 carbon atoms; respective $R^6$ and $R^7$ are an alkyl group of 1 to 6 carbon atoms, an alkenyl group of 2 to 6 carbon atoms, a cycloalkyl group of 3 to 7 carbon atoms, or a cycloalkenyl group of 5 to 7 carbon atoms; $R^6$ and $R^7$ may be combined with the neighboring carbon atom to represent a cycloalkyl group of 3 to 7 carbon atoms; a cycloalkenyl group of 5 to 7 carbon atoms, a bicycloalkyl group of 7 to 10 carbon atoms, or a bicycloalkenyl group of 7 to 10 carbon atoms; $R^2$ is an alkyl group of 1 to 6 carbon atoms; and $R^3$ is H, an alkyl group of 1 to 6 carbon atoms or an aralkyl group, or a pharmaceutically acceptable salt thereof. The compound has hypoglycemic, glucose tolerance improving and insulin sensitivity potentiating activities.

16 Claims, No Drawings

OXAZOLEACETIC ACID DERIVATIVES

This invention relates to novel oxazoleacetic acid derivatives which are of value as medicines.

More particularly, this invention relates to an oxazoleacetic acid derivative of the formula

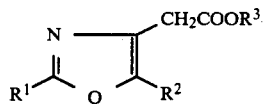 (I)

[$R^1$ is a group of the formula

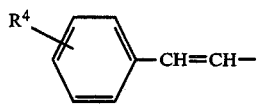

(where $R^4$ is a hydrogen atom, a halogen atom or a trifluoromethyl group) or a group of the formula

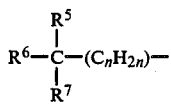

(where n is an integer of 0 to 3; $R^5$ is a hydrogen atom or a lower alkyl group; $R^6$ and $R^7$ are the same or different and each is a lower alkyl, lower alkenyl, cycloalkyl or cycloalkenyl group, or $R^6$ and $R^7$ taken together with the adjacent carbon atom form a cyclic group); $R^2$ is a lower alkyl group; and $R^3$ is a hydrogen atom or a lower alkyl or aralkyl group] or a salt thereof.

The research by the present inventors into the new oxazoleacetic acid derivative (I) led to the finding that this compound has hypoglycemic activity, glucose tolerance improving activity and insulin sensitivity potentiating activity, among others, in mammalian animals and accordingly is of value as an antidiabetic drug. This invention is based on the above finding.

Referring to the above formula (I), $R^1$ is a group of the formula

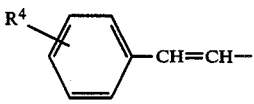 (A)

[wherein $R^4$ is a hydrogen atom, a halogen atom or a trifluoromethyl group] or a group of the formula

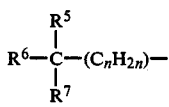 (B)

[where n is an integer of 0 to 3; $R^5$ is a hydrogen atom or a lower alkyl group; $R^6$ and $R^7$ are the same or different and each is a lower alkyl, lower alkenyl, cycloalkyl or cycloalkenyl group, or $R^6$ and $R^7$ taken together with the adjacent carbon atom form a cyclic group].

The (substituted) styryl group of formula (A) may be whichever of cis-and trans-forms but the trans-form is preferred. Referring to formula (A), the substituent group $R^4$ may be present at an optional position on the benzene ring, and the halogen may for example be fluorine, chlorine or bromine.

Referring to formula (B), the lower alkyl group $R^5$, $R^6$, $R^7$ is preferably a straight-chain or branched alkyl group of 1 to 6 carbon atoms, thus being exemplified by methyl, ethyl, propyl, isopropyl, butyl, isobutyl, secbutyl, tert-butyl, pentyl, isopentyl, neopentyl, tertpentyl, hexyl, isohexyl, etc. The cycloalkyl group $R^6$, $R^7$ is preferably a group of 3 to 7 carbon atoms, such as cyclopropyl, cyclobutyl, cyclopentyl, cyclohexyl, cycloheptyl, etc. The lower alkenyl and cycloalkenyl groups $R^6$, $R^7$ correspond respectively to the above alkyl and cycloalkyl groups, each containing a double bond in an optional position thereof. Thus, such lower alkenyl groups include those containing about 2 to 6 carbon atoms, such as vinyl, allyl, 1-propenyl, isopropenyl, 2-butenyl, 3-methyl-2-butenyl,3-pentenyl, 3-hexenyl, etc. The cycloalkenyl groups are those containing about 5 to 7 carbon atoms, such as 1-cyclopenten-1-yl, 2-cyclopenten-1-yl, 3-cyclopenten-1-yl, 1-cyclohexen-1-yl, 2-cyclohexen-1-yl, 3-cyclohexen-1-yl, 2,4-cyclohexadien-1-yl, 2-cyclohepten-1-yl, 3-cyclohepten-1-yl, etc.

When $R^6$ and $R^7$ taken together with the adjacent carbon atom form a cyclic group, the cyclic group includes the groups formed as two of the above-mentioned species of alkyl, alkenyl, cycloalkyl and cycloalkenyl are dehydrogenatedly combined at optional respective positions. Examplary species of said cyclic groups are those cycloalkyl and cycloalkenyl groups mentioned for $R^6$ and $R^7$, as well as bicycloalkyl and bicycloalkenyl groups. The bicycloalkyl groups preferably contain 7 to 10 carbon atoms, such as bicyclo[3,1,1]heptyl(norpinanyl), bicyclo[2,2,1]heptyl(norbornyl), bicyclo[3,2,1]octyl, bicyclo[2,2,2]octyl, bicyclo[4,3,0]nonyl, bicyclo[4,4,0]decyl, etc. The bicycloalkenyl groups are such that said bicycloalkyl groups have a double bond in an optional position, and are thus exemplified by bicyclo[3,1,1]hept-3-en-2-yl(3-norpinen-2-yl), bicyclo[2,2,1]hept-5-en-2-yl(5-norbonen-2-yl), bicyclo[3,2,1]oct-5-en-2-yl, bicyclo[2,2,2]oct-5-en-2-yl, bicyclo[4,3,0]non-4-en-2-yl, bicyclo[4,4,0]dec -4- en-2-yl, etc. The cycloalkyl, cycloalkenyl, bicycloalkyl, bicycloalkenyl, etc. as said substituents may have 1 to 3 alkyl substituents in optional positions.

In the formula (B), the case in which n of the —$C_nH_{2n}$— moiety is equal to 0 means that the oxazole ring is directly attached to

and the case in which n is equal to 1 through 3 means that they are attached to each other through an alkylene group of 1 through 3 carbon atoms, examples of the alkylene group being methylene, methylmethylene, ethylmethylene, ethylene, propylene, trimethylene, etc.

For $R^1$, a group of the formula (B) is generally preferable, and a group (B) wherein $R^5$ is a hydrogen atom or an alkyl of 1 to 3 carbon atoms, $R^6$ and $R^7$ taken together with the adjacent carbon atom form a cycloalkyl or cycloalkenyl group of 3 to 7 carbon atoms, and n is equal to 0 or 1 is particularly desirable.

Referring to formula (I), the lower alkyls $R^2$, $R^3$ may be the same straight-chain or branched alkyl groups as mentioned for $R^5$, $R^6$ and $R^7$. The aralkyl $R^3$ may be a phenyl-$C_{1-3}$alkyl (e.g. benzyl, phenylethyl, phenylpropyl, etc.). Generally, $R^2$ is preferably an alkyl group of 1 to 3 carbon atoms, particularly methyl, and $R^3$ is preferably a hydrogen atom.

The contemplated compound of this invention can be produced, for example, by the following processes.

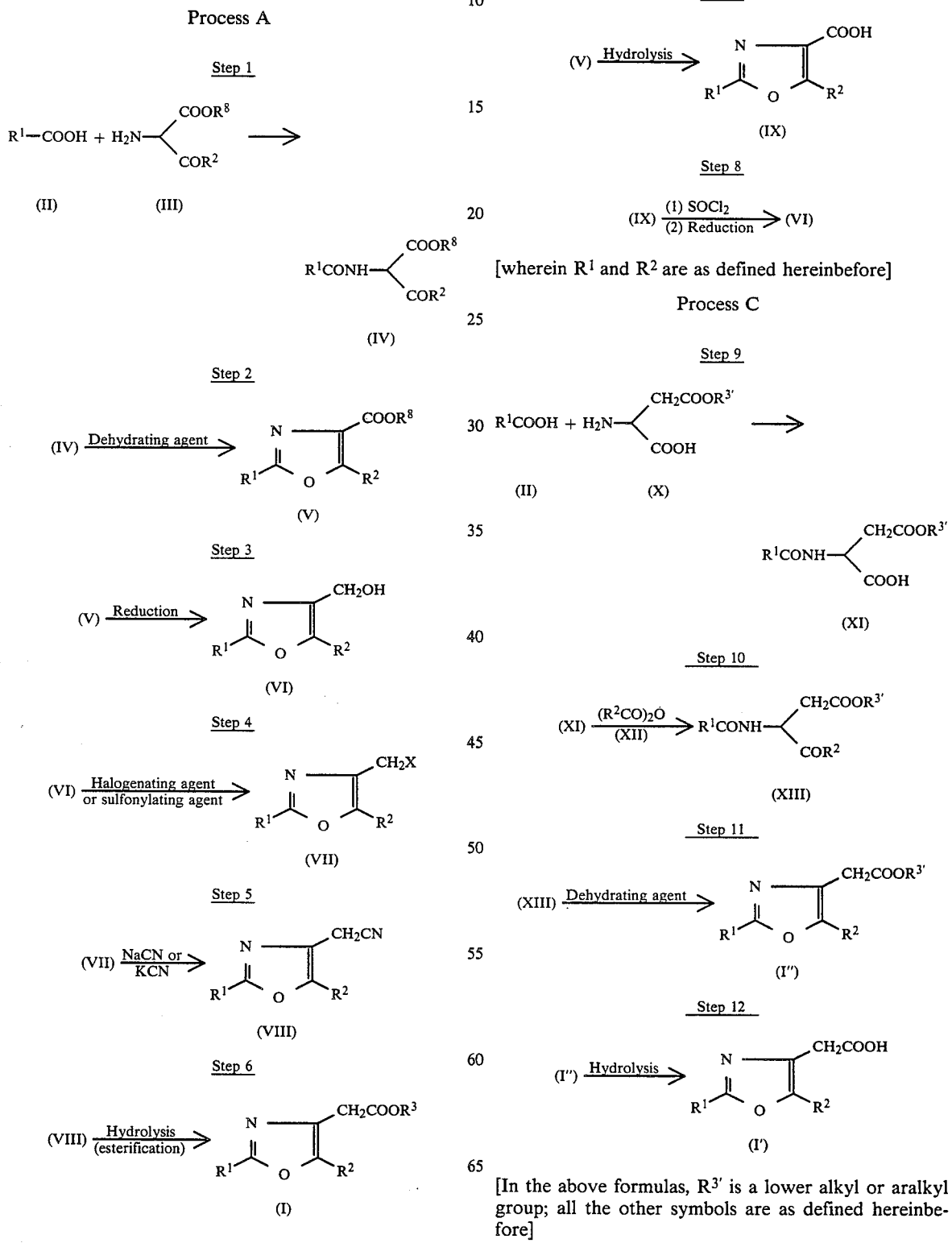

[In the above formulas, $R^1$, $R^2$ and $R^3$ are as defined hereinbefore; $R^8$ is a lower alkyl or aralkyl group; X is a leaving group]

Process B

Instead of Step 3 in Process A, the following Step 7 and Step 8 are employed.

[wherein $R^1$ and $R^2$ are as defined hereinbefore]

[In the above formulas, $R^{3'}$ is a lower alkyl or aralkyl group; all the other symbols are as defined hereinbefore]

Referring to the above formulas, the lower alkyl and aralkyl groups $R^8$, $R^{3'}$ are similar to those mentioned by way of example for $R^3$. The leaving group X may for example be a halogen atom (e.g. chlorine, bromine, iodine) or a sulfonyloxy group (e.g. mesyloxy, tosyloxy, benzenesulfonyloxy).

Each of the above production processes will be described in detail.

Process A

Step 1

In the first place, a compound (III) is reacted with a carboxylic acid (II) or a reactive derivative thereof to give a compound (IV). This acylation reaction can be conducted in the conventional manner; direct condensation of (II) and (III) with the aid of dicyclohexylcarbodiimide, or reaction of (III) with a reactive derivative of (II) such as the acid anhydride, acid halide (e.g. acid chloride, acid bromide), imidazolide or mixed acid anhydride (e.g. anhydrides with monomethyl carbonate, monoethyl carbonate, monoisobutyl carbonate, etc.). Of these known methods, the most expedient is the method employing an acid halide or mixed acid anhydride of (II). The reaction using an acid halide is conducted generally in a solvent (e.g. chloroform, dichloromethane, ethyl acetate, tetrahydrofuran, water, and mixtures thereof) in the presence of a base (e.g. triethylamine, N-methylmorpholine, sodium hydrogen carbonate, potassium hydrogen carbonate, sodium carbonate, potassium carbonate) at a temperature of $-10°$ to $+30°$ C. Based on each mole of (III), the acid halide is used in an amount of 1 to 1.2 moles. When a mixed acid anhydride is employed, (II) is preferably first reacted with a chlorocarbonic acid ester (e.g. methyl chlorocarbonate, ethyl chlorocarbonate, isobutyl chlorocarbonate, etc.) or the like in the presence of a base (e.g. triethylamine, N-methylmorpholine, etc.) in a suitable solvent (e.g. chloroform, dichloromethane, ethyl acetate, tetrahydrofuran, etc.) at $-10°$ to $+10°$ C. The mixed acid anhydride thus prepared is then reacted with (III) at $-10°$ to $+30°$ C. The preferred amount of mixed acid anhydride is 1 to 1.2 moles per mole of (III).

Step 2

(IV) is cyclized with a dehydrating agent to give (V). The dehydrating agent for this reaction may be selected from among the known compounds such as pohsphorus oxychloride, thionyl chloride, phosphorus pentoxide, polyphosphoric acid, polyphosphoric acid esters, acetic anhdydride, sulfuric acid, etc. and mixtures thereof. While the reaction conditions may vary with different kinds of dehydrating agents, this reaction can be generally conducted in an appropriate inert solvent (e.g. benzene, toluene, xylene, chloroform, dichloromethane, etc.) at 30° to 140° C. or in an excess of a dehydrating agent where the same agent functions as a reaction solvent as well, at a similar temperature. The proportion of the dehydrating agent is 1 to 30 moles per mole of (IV).

Step 3

(V) is reduced to (VI). This reduction reaction can be easily carried out with a reducing agent such as lithium aluminum hydride, sodium dihydro-bis(2-methoxyethoxy)aluminate, etc. Generally, this reaction is preferably conducted in a solvent such as ethyl ether, tetrahydrofuran, dimethoxyethane, benzene, toluene, etc. using 1 to 2 moles of said reducing agent per mole of (V) at a temperature from $-10°$ C. to the boiling point of the solvent.

Step 4

(VI) is reacted with a halogenating agent or a sulfonylating agent to give (VII). The halogenating agent is preferably thionyl chloride or phosphorous tribromide, for instance, and the reaction in this case yields (VII) wherein X is chlorine or bromine. This reaction is conducted in an appropriate inert solvent (e.g. benzene, toluene, xylene, chloroform, dichloromethane, etc.) or using the halogenating agent in such an excess as allows it to serve as a solvent, at a temperature in the range of $-10°$ to $+80°$ C. The amount of halogenating agent is 1 to 20 moles per mole of (VI). Preferred examples of the sulfonylating agent include mesyl chloride, tosyl chloride, benzenesulfonyl chloride, etc. and the reaction in such cases yields (VII) wherein X is mesyloxy, tosyloxy, or benzenesulfonyloxy as the case may be. This reaction is generally conducted in a solvent inert thereto (e.g. benzene, toluene, xylene, ethyl ether, ethyl acetate, tetrahydrofuran, chloroform, dichloromethane, etc,) in the presence of a base (e.g. triethylamine, N-methylmorpholine, etc.) at a temperature of $-10°$ to $+30°$ C. The amount of such sulfonylating agent and of such base is 1 to 1.2 moles each per mole of (VI). The compound (VII) wherein X is iodine can be produced by reacting 1 mole of the thus-produced compound (VII) wherein X is chlorine, bromine or sulfonyloxy with 1 to 1.2 moles of sodium iodide or potassium iodide. This reaction can be conducted in a solvent such as acetone, methyl ethyl ketone, methanol, ethanol, etc. at a temperature of 20° to 80° C.

Step 5

(VII) is reacted with sodium cyanide or potassium cyanide to produce (VIII). This reaction is conducted by adding sodium cyanide or potassium cyanide to (VII) in a suitable solvent. The solvent may for example be methanol, ethanol, dimethylformamide or dimethyl sulfoxide. While this reaction is generally carried out in the neighborhood of room temperature, it may be conducted at a suitable elevated temperature. The amount of sodium cyanide or potassium cyanide is 1 to 3 moles per mole of (VII). When Y in (VII) is other than iodine, 0.1 to 1 mole of sodium iodide or potassium iodide may be added to the reaction system so as to hasten the reaction.

Step 6

The cyano group of (VIII) is hydrolyzed and, if necessary, further esterified to give (I). This hydrolysis reaction can be easily performed by using an alkali such as sodium hydroxide or potassium hydroxide. The reaction is preferably conducted in a solvent such as methanol, ethanol etc. and in the presence of said alkali or an aqueous solution thereof, at a temperature near the boiling point of the solvent used. The amount of said alkali is 2 to 6 moles and preferably 3 to 4 moles per mole of (VIII). The resulting carboxylic acid ($R^3$=H) can be converted to an ester ($R^3$=lower alkyl or aralkyl) if necessary. This esterification reaction can be carried out by the per se known reaction, e.g. by using diazomethane, alcohol and acid (e.g. hydrochloride, sulfuric acid, p-toluenesulfonic acid, etc.) or thionyl chloride and alcohol.

Production Process B

In case the yield of (VI) obtainable by the reduction of (V) is low in Step 3 of Production Process A, it is advantageous to produce (VI) by Step 7 and Step 8 of this Production Process B.

Step 7

(V) is hydrolyzed to (IX). This hydrolysis reaction can be easily carried out using an alkali such as sodium hydroxide or potassium hydroxide in water, methanol or ethanol or a mixture thereof, for instance. This reaction is generally conducted at 20° to 100° C., and the amount of said alkali is 1 to 5 moles per mole of (V).

Step 8

In this step, (IX) is first treated with thionyl chloride to give an acid chloride of the formula

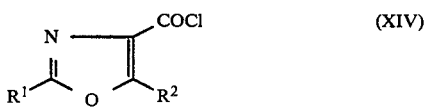

[$R^1$ and $R^2$ are as defined hereinbefore] which is then reduced to (VI). The reaction of (IX) with thionyl chloride is generally performed using an excess of thionyl chloride as a solvent under reflux conditions, although it may be conducted in a suitable inert solvent (e.g. benzene, toluene, xylene, dichloromethane, chloroform, etc.). The reaction temperature is preferably the boiling point of the solvent used. The amount of thionyl chloride is 1 to 20 moles per mole of (IX).

The (XIV) thus obtained is generally not purified but directly reduced to (VI). This reduction reaction is preferably conducted using sodium borohydride. This reaction is preferably carried out in an ether solvent such as tetrahydrofuran, dioxane, dimethoxyethane, diethoxyethane, etc. at −10° to +20° C. The amount of sodium borohydride is 1 to 3 moles per mole of (XIV).

(III), which is the starting material for these Production Processes A and B, is either a known compound or a compound which can be easily synthesized by the konwn process [e.g. S. Gabriel et al.: Chem. Ber. 27, 1141 (1894).]

Production Process C

Step 9

An aspartic acid β-ester (X) is acylated to (XI). This acylation reaction is conducted substantially in the same manner as Step I of Production Process A but since the starting material (X) contains a free carboxyl group, a base required for its neutralization is additionally employed.

Step 10

(XI) is subjected to Dakin-West reaction [e.g. W. Steglich et al.: Chem. Ber. 102, 883 (1969); G. Höfle et al., Chem. Ber. 105, 1718 (1972), etc.] to produce (XIII). For this reaction, (XI) is preferably reacted with acid anhydride (XII) in the presence of a base. The base is preferably pyridine, triethylamine, N-methylmorpholine or the like. Addition of a catalytic amount (0.01 to 0.1 mol. equiv.) of 4-dimethylaminopyridine results in improvements in reaction rate and yield. This reaction is generally conducted at 10 to 100° C. using an excess of (XII) or the base as a solvent. However, the reaction may be carried out in a solvent inert thereto (e.g. benzene, toluene, tetrahydrofuran, dioxane, dimethoxyethane, etc.). The amount of (XII) is generally 4 to 12 moles per mole of (XI), and the amount of said base is 3 to 10 moles. In this reaction, a compound of formula (XV)

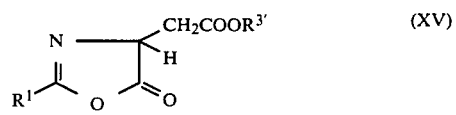

[$R^1$ and $R^{3'}$ are as defined hereinbefore] is first produced as an intermediate compound and this intermediate is subsequently acylated to (XVI):

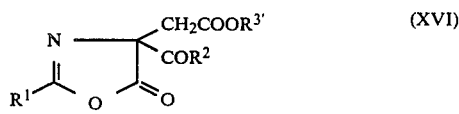

[$R^1$, $R^2$ and $R^{3'}$ are as defined hereinbefore]. Then, probably due to the action of carboxylic acid present in the reaction mixture and/or owing to the treatment of the reaction mixture with water, fission of the oxazolone ring and a decarboxylation reaction take place to give (XIII).

Therefore, it is generally unnecessary to isolate (XV), (XVI), etc., although such isolation procedures may be interposed in certain cases.

Step 11

Using a dehydrating agent, (XIII) is cyclized to give (I″), which is the desired compound (I) wherein $R^3$ is a lower alkyl or aralkyl group. This reaction can be conducted substantially under the same conditions as Step 2 of Production Process A.

Step 12

(I″) is hydrolyzed to (I′), i.e. the desired compound (I) wherein $R^3$ is a hydrogen atom. This hydrolysis reaction can be conducted substantially under the same conditions as Step 7 of Production Process B, and the product compound (I′) can be esterified, if desired, in the same manner as Step 6 of Production Process A.

Of the compounds produced by the above Production Processes A through C, the compound wherein the group $R^1$ contains an alkenyl, cycloalkenyl or bicycloalkenyl group can be catalytically reduced to give the corresponding alkyl, cycloalkyl or bicycloalkyl group $R^1$. Such catalytic reduction can be carried out in a suitable solvent (e.g. methanol, ethanol, ethyl acetate, etc.) using a catalyst such as palladium-on-carbon, platinum oxide, etc. at atmospheric temperature and pressure.

When the compound [I] obtained in the above-described manner is a free carboxylic acid ($R^3$=H), it can be converted to a pharmaceutically acceptable salt with a base by the conventional procedure. The salt may for example be the salt with sodium, potassium, aluminum or calcium, for instance. Moreover, when the group $R^1$ contains a stereoisomer or optical isomer, for example, such isomers either severally or as a mixture fall within the scope of this invention.

The compounds (I) and salts according to this invention are novel compounds which have not been described in the literature to this day and as these compounds and salts have hypoglycemic activity, glucose tolerance improving activity, insulin sensitivity potentiating activity, etc. and are of low toxicity, they are of value as drugs for the treatment of diabetes. When the compound of this invention is used as an antidiabetic, it can be safely administered orally or by other routes of administration, in the form of pharmaceutical preparations containing a pharmaceutically acceptable carrier, excipient or diluent, such as powders, granules, tablets, capsules, and injections. The dosage of (I) for a diabetic patient depends on the severity of the disease and other factors. However, the daily oral dose for an adult human is generally about 1 mg to about 30 mg per kg body weight and preferably about 2 mg to about 20 mg on the same basis. The above amount is preferably administered in 2 to 3 divided doses daily. The results of pharmacological tests demonstrating the usefulness of compounds of this invention are given below.

1. Insulin sensitivity potentiating effect in mice Biological assay:

The insulin sensitivity test by the following method was conducted to investigate the insulin sensitivity potentiating activity of the test compound. This study was carried out in male ICR mice aged 7 to 9 weeks which had been kept on CE-2 diet (CLEA JAPAN). Each of the ICR mice (in groups of 5 individuals) was orally dosed with 100 mg/kg of each test compound (as suspended in 5% gum arabic solution) by gastric gavage and fasted overnight (20 hrs.) Next morning, a further 100 mg/kg dose of the same compound was administered. A control group was given a 5% solution of gum arabic. Thirty minutes after the second treatment, 0.1 U/kg of insulin (Regular, Novo) was intraperitoneally administered. At 0, 60 and 120 minutes after administration of insulin, the blood was taken from the orbital venus plexus and the blood glucose level was determined. This glucose determination was carried out enzymatically by the glucose oxidase method. The activity of the test compound was express in the percent fall of blood glucose level with respect to the non-treatment group control.

Results:

The results are set forth in Table 1.

TABLE 1

| Compound (Example No.) | Decrease of blood glucose (%) | | |
|---|---|---|---|
| | After 0 min. | After 60 min. | After 120 min. |
| 1 | 26 | 38 | 34 |
| 2 | 25 | 51 | 30 |
| 5 | 24 | 40 | 25 |
| 9 | 22 | 24 | 32 |
| 10 | 47 | 49 | 53 |
| 11 | 39 | 40 | 60 |
| 12 | 34 | 36 | 44 |
| 19 | 47 | 46 | 46 |
| 20 | 39 | 28 | 27 |
| 21 | 11 | 22 | 40 |
| 22 | 40 | 18 | 36 |
| 23 | 43 | 52 | 57 |
| 24 | 40 | 44 | 46 |
| 25 | 32 | 44 | 56 |

2. Hypoglycemic effect

Procedure:

Using diabetic KK-A$^y$ mice with hereditary obesity (aged 10 to 13 weeks, 5 mice/group), the effect of the test compound on the glucose level of fasted blood was investigated. Each KK-A$^y$ mouse fasted for 18 to 20 hours was orally dosed with [2-(1-methylcyclohexyl)-5-methyl-4-oxazoleacetic acid (as suspended in 5% gum arabic) by gastric gavage and at 0, 60 and 120 minutes after the treatment, the blood was taken from the orbital venus plexus and the blood glucose level was determined. Thus, the blood concentration of glucose was measured by the glucose oxidase method. Results:

It will be apparent from Table 2 that the blood glucose lowering effect of the compound in the fasted KK-A$^y$ mouse was dose-dependent and sustained for more than 120 minutes.

TABLE 2

| | Dose (mg/kg P.O.) | Blood glucose (mg/dl) | | |
|---|---|---|---|---|
| | | 0 min. | 60 min. | 120 min. |
| Control group | — | 131 ± 17 | 139 ± 13 | 111 ± 11 |
| Test groups | 10 | 136 ± 13 | 131 ± 11 | 109 ± 8 |
| | 20 | 131 ± 13 | 111 ± 11 | 98 ± 9 |
| | 50 | 124 ± 13 | 89 ± 14 | 88 ± 14 |

3. Glucose tolerance improving effect

Procedure:

The glucose tolerance improving effect of the test compound was studied in male hereditary fatty rats with glucose intolerance (aged 9 to 10 weeks, 5 animals/group). Each fatty rat fasted for 20 hours was orally dosed with 100 mg/kg of 2-(1-methylcyclohexyl)-5-methyl-4-oxazoleacetic acid (as suspended in 5% gum arabic) and 30 minutes after the treatment 2 g/kg of glucose was orally administered. At 0, 30, 60 and 120 minutes after the glucose loading, the blood was taken from the tail vein and the blood glucose and plasma insulin levels were determined.

Results:

The blood glucose level was significantly reduced as compared with control. Thus, the blood glucose concentration at 0, 30 and 60 minutes were 78, 75 and 70%, respectively, relative to control. On the other hand, there was no significant difference in insulin secretion response between the groups.

This invention will be described in further detail by way of the following examples and preparation examples, it being understood that the invention is by no means limited thereto.

EXAMPLE 1

(1) Triethylamine (8.3 ml) was added dropwise to a solution of ethyl 2-aminoacetoacetate hydrochloride (5.43 g) and cinnamoyl chloride (5.0 g) in chloroform (90 ml) with ice-cooling and stirring. After 20 minutes, the mixture was washed with water and dried over anhydrous magnesium sulfate. The solvent was then distilled off and the residue was treated with isopropyl ether to give ethyl 2-cinnamoylaminoacetoacetate as crystals; yield 6.1 g (73.9%). Recrystallization from ethanol gave colorless needles melting at 113°–114° C.

Elemental analysis; Calcd. for $C_{15}H_{17}NO_4$: C, 65.44; H, 6.22; N, 5.09; Found: C, 65.55; H, 6.08; N, 5.01.

(2) A mixture of ethyl 2-cinnamoylaminoacetoacetate (5.7 g) and phosphorus oxychloride (40 ml) was heated on an oil bath at 100°–110° C. for 30 minutes and the phosphorus oxychloride was distilled off under reduced pressure. The residue was neutralized with aqueous sodium hydrogen carbonate and extracted with chloroform. The chloroform layer was washed with water and dried over anhydrous magnesium sulfate. The solvent was then distilled off and the residue was treated with hexane to give ethyl 5-methyl-2-styryl-4-oxazolecarboxylate as crystals; yield 4.3 g (80.7%). Recrystallization from ethanol gave light-yellow prisms melting at 98°–99° C.

Elemental analysis; Calcd. for $C_{15}H_{15}NO_3$: C, 70.02; H, 5.88; N, 5.44; Found: C, 69.81; H, 5.79; N, 5.37.

(3) Ethyl 5-methyl-2-styryl-4-oxazolecarboxylate (2.14 g) was dissolved in a mixture of dry tetrahydrofuran (10 ml) and dry ethyl ether (15 ml) and the solution was added dropwise to a suspension of lithiumaluminum hydride (0.34 g) in dry ethyl ether (20 ml) with ice-cooling and stirring. The mixture was further stirred under ice-cooling for an hour and water (2 ml) was added portionwise for decomposition. The precipitate was filtered off and the filtrate was concentrated to give 4-hydroxymethyl-5-methyl-2-styryloxazole as crystals; yield 1.28 g (71.5%). Recrystallization from acetone gave colorless prisms melting at 106°–107° C.

Elemental analysis; Calcd. for $C_{13}H_{13}NO_2$: C, 72.54; H, 6.09; N, 6.51; Found: C, 72.46; H, 6.01; N, 6.22.

(4) 4-Hydroxymethyl-5-methyl-2-styryloxazole (1.0 g) was added to thionyl chloride (3 ml) and the mixture was allowed to stand at room temperature for 30 minutes. The thionyl chloride was distilled off under reduced pressure. The residue was neutralized with aqueous sodium hydrogen carbonate and extracted with ethyl acetate. The ethyl acetate layer was washed with water and dried over anhydrous magnesium sulfate. The solvent was then distilled off and isopropyl ether was added to the residue to give 4-chloromethyl-5-methyl-2-styryloxazole as crystals; yield 0.98 g (90.7%). Recrystallization from ether gave light-yellow plates melting at 108°–109° C.

Elemental analysis; Calcd. for $C_{13}H_{12}ClNO$: C, 66.81; H, 5.18; N, 5.99; Found: C, 67.07; H, 5.16; N, 6.08.

(5) A solution of 4-chloromethyl-5-methyl-2-styryloxazole (2.33 g) in dimethyl sulfoxide (10 ml) was added dropwise to a solution of sodium cyanide (0.59 g) in dimethyl sulfoxide with stirring. The mixture was stirred for 1.5 hours and then diluted with ice water to give 4-cyanomethyl-5-methyl-3-styryloxazole as crystals; yield 2.10 g (93.8%). Recrystallization from isopropanol gave colorless prisms melting at 72°–73° C.

Elemental analysis; Calcd. for $C_{14}H_{12}N_2O$: C, 74.98; H, 5.39; N, 12.49; Found: C, 74.82; H, 5.18; N, 12.27.

(6) 4-Cyanomethyl-5-methyl-3-styryloxazole (1.8 g) was added to a mixture of ethanol (25 ml) and 2N sodium hydroxide (20 ml). The whole mixture was refluxed with stirring for 3 hours, concentrated to about half of its original volume, diluted with water and acidified with acetic acid to give 5-methyl-2-styryl-4-oxzazoleacetic acid; yield 1.75 g (89.7%). Decoloration with activated carbon and recrystallization from acetone gave pale brown needles melting at 182°–183° C. Yield 1.40 g (71.8%).

Elemental analysis; Calcd. for $C_{14}H_{13}NO_3$: C, 69.12; H, 5.39; N, 5.76; Found: C, 69.10; H, 5.40; N, 5.69.

EXAMPLE 2

(1) To a suspension of o-chlorocinnamic acid (9.1 g) in dichloromethane (200 ml) was added triethylamine (21 ml) for dissolution. With cooling with ice-sodium chloride and stirring, ethyl chlorocarbonate (5.0 ml) was added dropwise to the above-obtained solution, and the mixture was further stirred for 10 minutes. To the resulting mixed acid anhydride solution was added portionwise ethyl 2-aminoacetoacetate hydrochloride (9.05 g) and the mixture was stirred under cooling for 20 minutes and at room temperature for 40 minutes. The reaction mixture was washed with diluted hydrochloric acid, water, aqueous sodium hydrogen carbonate and water in that order and dried over anhydrous magnesium sulfate. The solvent was then distilled off and the residue was dissolved in toluene (100 ml). Phosphorus oxychloride (14 ml) was added and the mixture was refluxed for an hour. The solvent and phosphorus oxychloride were distilled off under reduced pressure, and the residue was neutralized with aqueous sodium hydrogen carbonate and extracted with ethyl ether. The ethyl ether layer was washed with water and dried over anhydrous magnesium sulfate. The solvent was distilled off and the residue was treated with isopropyl ether to give ethyl 2-(2- chlorostyryl)-5-methyl-4-oxazolecarboxylate as crystals; yield 6.4 g (44.1%). Recrystallization from ethanol gave yellow prisms melting at 99°–100° C.

Elemental analysis; Calcd. for $C_{15}H_{14}ClNO_3$: C, 61.76; H, 4.84; N, 4.80; Found: C, 61.58; H, 4.69; N, 4.90.

(2) Ethyl 2-(2-chlorostyryl)-5-methyl-4-oxazolecarboxylate (6.0 g) was added to a mixture of ethanol (42 ml) and 2N sodium hydroxide (21 ml) and the whole mixture was heated on a water bath at 100° C. for dissolution. New crystals (sodium salt) immediately precipitated out. They were dissolved by addition of water and the solution was acidified with acetic acid to give 2-(2-chlorostyryl)-5-methyl-4-oxazolecarboxylic acid as crystals; yield 5.2 g (96.3%). Recrystallization from acetic acid-water gave colorless needles. melting at 223°–224° C.

Elemental analysis; Calcd. for $C_{13}H_{10}ClNO_3$: C, 59.22; H, 3.82; N, 5.37; Found: C, 59.05; H, 3.74; N, 5.14.

(3) A mixture of 2-(2-chlorostyryl)-5-methyl-4-oxazolecarboxylic acid (4.8 g) and thionyl chloride (24 ml) was refluxed with stirring for an hour. The thionyl chloride was distilled off and the crystalline residue (acid chloride) was washed with isopropyl ether and dissolved in dimethoxyethane (20 ml). The solution was added dropwise to a suspension of sodium borohydride (1.4 g) in dimethoxyethane (30 ml) with ice-cooling and stirring. The reaction was allowed to proceed under ice-cooling for 30 minutes and the reaction mixture was adjusted to pH 2 with 2N hydrochloric acid and refluxed for 30 minutes. The solvent was then distilled off and the residue was neutralized with aqueous sodium hydrogen carbonate and extracted with ethyl acetate. The ethyl acetate layer was washed with water and dried over anhydrous magnesium sulfate. The solvent was distilled off and the resulting crystalline precipitate was collected by filtration and washed with isopropyl ether to give 2-(2-chlorostyryl)-4-hydroxymethyl-5-methyloxazole; yield 3.9 g (85.9%). Recrystallization from ethanol gave colorless needles melting at 122°–123° C.

Elemental analysis; Calcd. for $C_{13}H_{12}ClNO_2$: C, 62.53; H, 4.84; N, 5.61; Found: C, 62.49; H, 4.64; N, 5.75.

(4) 2-(2-Chlorostyryl)-4-hydroxymethyl-5-methyloxazole (3.6 g) was added portionwise to thionyl chloride (18 ml) with ice-cooling and stirring. The mixture was stirred at room temperature for 20 minutes and the thionyl chloride was distilled off. To the residue was added aqueous sodium hydrogen carbonate and the mixture was extracted with ethyl acetate. The ethyl acetate layer was washed with water and dried over anhydrous magnesium sulfate. The solvent was then distilled off to give 4-chloromethyl-2-(2-chlorostyryl)-5-methyloxazole as crystals; yield 3.65 g (99.5%). Recrystallization from ethyl ether gave colorless needles melting at 109°–110° C.

Elemental analysis; Calcd. for $C_{13}H_{11}Cl_2NO$: C, 58.23; H, 4.14; N, 5.22; Found: C, 58.11; H, 4.08; N, 5.45.

(5) 4-Chloromethyl-2-(2-chlorostyryl)-5-methyloxazole was reacted with sodium cyanide in the same manner as Example 1-(5) to give 2-(2-chlorostyryl)-4-cyanomethyl-5-methyloxazole. Yield 96.9%. Light-yellow needles (recrystallized from ethanol). Mp 89°–90° C.

Elemental analysis; Calcd. for $C_{14}H_{11}ClN_2O$: C, 65.00; H, 4.29; N, 10.83; Found: C, 65.20; H, 4.19; N, 10.77.

(6) 2-(2-Chlorostyryl)-4-cyanomethyl-5-methyloxazole was hydrolyzed in the same manner as Example 1-(6) to give 2-(2-chlorostyryl)-5-methyl-4-oxazoleacetic acid. Yield 93.2%. Pale brown needles (recrystallized from ethyl acetate). Mp 148°–149° C.

Elemental analysis; Calcd. for $C_{14}H_{12}ClNO_3$: C, 60.55; H, 4.36; N, 5.04; Found: C, 60.34; H, 4.27; N, 5.06.

In the same manner as Example 2, the following compounds (listed in Examples 3–5) were obtained. For intermediates, only those that were isolated in the form of crystals are listed.

EXAMPLE 3

(1) Ethyl 2-(4-chlorocinnamoylamino)acetoacetate: yield 62.3%, mp 119°°120° C. (recrystallized from ethanol).

(2) Ethyl 2-(4-chlorostyryl)-5-methyl-4-oxazolecarboxylate: Yield 79.4%, mp 105°–106° C. (recrystallized from ethanol).

(3) 2-(4-Chlorostyryl)-5-methyl-4-oxazolecarboxylic acid: Yield 89.8%, mp 244°–245° C. (recrystallized from acetone).

(4) 2-(4-Chlorostyryl)-4-hydroxymethyl-5-methyloxazole: Yield 88.4%, mp 129°–130° C. (recrystallized from ethanol).

(5) 4-Chloromethyl-2-(4-chlorostyryl)-5-methyloxazole: Yield 92.8%, mp 121°–122° C. (recrystallized from ethanol).

(6) 2-(4-Chlorostyryl)-4-cyanomethyl-5-methyloxazole: Yield 98.4%, mp 124°–125° C. (recrystallized from ethanol).

(7) 2-(4-Chlorostyryl)-5-methyl-4-oxazoleacetic acid: Yield 83.7%, mp 157°–158° C. (recrystallized from ethyl acetate).

Elemental analysis; Calcd. for $C_{14}H_{12}ClNO_3$: C, 60.55; H, 4.36; N, 5.04; Found: C, 60.61; H, 4.63; N, 4.99.

EXAMPLE 4

(1) Ethyl 2-(3-chlorostyryl)-5-methyl-4-oxazolecarboxylate: Yield 51.7%, mp 116°–117° C. (recrystallized from ethanol).

(2) 2-(3-Chlorostyryl)-5-methyl-4-oxazolecarboxylic acid: Yield 98.4%, mp 213°–214° C. (recrystallized from acetone).

(3) 2-(3-Chlorostyryl)-4-hydroxymethyl-5-methyloxazole: Yield 83.3%, mp 147°–148° C. (recrystallized from ethanol).

(4) 4-Chloromethyl-2-(3-chlorostyryl)-5-methyloxazole: Yield 90.7%, mp 86°–87° C. (recrystallized from isopropyl ether).

(5) 2-(3-Chlorostyryl)-4-cyanomethyl-5-methyloxazole: Yield 96.9%, mp 119°–120° C. (recrystallized from ethanol).

(6) 2-(3-Chlorostyryl)-5-methyl-4-oxazoleacetic acid: Yield 93.2%, mp 214°–215° C. (recrystallized from dichloromethane-methanol).

Elemental analysis; Calcd. for $C_{14}H_{12}ClNO_3$: C, 60.55; H, 4.36; N, 5.04; Found: C, 60.56; H, 4.31; N, 5.09.

EXAMPLE 5

(1) Ethyl 5-methyl-2-(3-trifluoromethylstyryl)-4-oxazolecarboxylate: Yield 26.5%, mp 103°–104° C. (recrystallized from ethanol).

(2) 5-Methyl-2-(3-trifluoromethylstyryl)-4-oxazolecarboxylic acid: Yield 99.4%, mp 204°–205° C. (recrystallized from acetic acid-water).

(3) 4-Hydroxymethyl-5-methyl-2-(3-trifluoromethylstyryl)oxazole: Yield 65.5%, mp 134°–135° C. (recrystallized from ethanol).

(4) 4-Chloromethyl-5-methyl-2-(3-trifluoromethylstyryl)oxazole: Yield 88.5%, mp 99°–100° C. (recrystallized from isopropyl ether).

(5) 4-Cyanomethyl-5-methyl-2-(3-trifluoromethylstyryl)oxazole: Yield 95.9%, mp 107°–108° C. (recrystallized from ethanol).

(6) 5-Methyl-2-(3-trifluoromethylstyryl)-4-oxazoleacetic acid: Yield 80.3%, mp 157°–158° C. (recrystallized from ethanol).

Elemental analysis; Calcd. for $C_{15}H_{12}F_3NO_3$: C, 57.88; H, 3.89; N, 4.50; Found: C, 57.55; H, 3.80; N, 4.60.

EXAMPLE 6

(1) Sodium hydrogen carbonate (10.0 g) was added to a mixture of methyl 2-amino-3-oxovalerate hydrochloride (9.1 g), ethyl acetate (50 ml) and water (40 ml) with ice-cooling and stirring followed by dropwise addition of a solution of cinnamoyl chloride (8.3 g) in ethyl acetate (10 ml). The whole mixture was stirred under ice-cooling for 2 hours and the ethyl acetate layer was separated. The aqueous layer was extracted with ethyl acetate. The ethyl acetate layers were combined, washed with water and dried over anhydrous magnesium sulfate. The solvent was then distilled off and isopropyl ether was added to the residue to give methyl 2-cinnamoylamino-3-oxovalerate as crystals; yield 8.8 g (63.8%). Recrystallization from ethanol gave colorless needles melting at 119°–120° C.

Elemental analysis; Calcd. for $C_{15}H_{17}NO_4$: C, 65.44; H, 6.22; N, 5.09; Found: C, 65.54; H, 6.09; N, 5.13.

(2) A mixture of methyl 2-cinnamoylamino-3-oxovalerate (8.25 g), phosphorus oxychloride (5.6 ml) and toluene (80 ml) was refluxed with stirring for 40 minutes. The solvent was then distilled off and the residue was neutralized with aqueous sodium hydrogen carbonate and extracted with ethyl ether. The ethyl ether layer was washed with water and dried over anhydrous magnesium sulfate. The solvent was distilled off and the oily residue was dissolved in ethanol (30 ml). To the solution was added 2N sodium hydroxide (30 ml) and the mixture was heated on a water bath at 90° C. for 5 minutes. After cooling, the reaction mixture was adjusted to pH 2 with 2N hydrochloric acid and diluted with water. The resulting crystalline precipitate was collected by filtration to give 5-ethyl-2-styryl-4oxazolecarboxylic acid; yield 7.12 g (97.7%). Recrystallization from ethanol gave colorless prisms melting at 143°–144° C.

Elemental analysis; Cacld for $C_{14}H_{13}NO_3$: C, 69.12; H, 5.39; N, 5.76; Found: C, 69.15; H, 5.31; N, 5.75.

(3) A mixture of 5-ethyl-2-styryl-4-oxazolecarboxylic acid (5.57 g) and thionyl chloride (17 ml) was refluxed with stirring for an hour and the thionyl chloride was completely distilled off. The residue was dissolved in dimethoxyethane (20 ml) and the solution was added dropwise to a mixture of sodium borohydride (1.74 g) and dimethoxyethane (50 ml) under cooling with ice-sodium chloride and stirring. The whole mixture was stirred for 15 minutes, adjusted to pH 2 with 2N hydrochloric acid and refluxed for 30 minutes. The reaction mixture was concentrated, neutralized with aqueous sodium hydrogen carbonate and extracted with ethyl acetate. The ethyl acetate layer was washed with water and dried over anhydrous magnesium sulfate. The solvent was then distilled off and the residue was treated with hexane to give 5-ethyl-4-hydroxymethyl-2-styryloxazole as crystals; yield 4.37 g (83.4%). Recrystallization from ethyl ether gave colorless prisms melting at 90°–91° C.

Elemental analysis; Calcd. for $C_{14}H_{15}NO_2$: C, 73.34; H, 6.59; N, 6.11; Found: C, 73.08; H, 6.59; N, 6.31.

(4) 5-Ethyl-4-hydroxymethyl-2-styryloxazole (2.3 g) was added portionwise to thionyl chloride (11.5 ml) with ice-cooling and stirring and the mixture was stirred for 15 minutes. The thionyl chloride was distilled off and the residue was neutralized with aqueous sodium hydrogen carbonate and extracted with ethyl acetate. The ethyl acetate layer was washed with water and dried over anhydrous magnesium sulfate. The solvent was distilled off and the residue was dissolved in dimethyl sulfoxide (20 ml). Sodium cyanide (0.58 g) was added with ice-cooling and stirring and the mixture was further stirred at room temperature for 2 hours, diluted with ice water and extracted with ethyl ether. The ethyl ether layer was washed with water and dried over anhydrous magnesium sulfate. The solvent was then distilled off and ethanol (25 ml) and 2N sodium hydroxide (25 ml) were added to the residue. The mixture was refluxed with stirring for 3 hours, diluted with water, washed with ethyl ether and acidified with hydrochloric acid. The resulting crystalline precipitate was collected by filtration to give 5-ethyl-2-styryl-4-oxazoleacetic acid; yield 1.51 g (58.8%). Recrystallization from ethanol gave colorless needles melting at 164°–165° C.

Elemental analysis; Calcd. for $C_{15}H_{15}NO_3$: C, 70.02; H, 5.88; N, 5.44; Found: C, 70.32; H, 5.83; N, 5.46.

Proceeding in the same manner as Example 6 but using the corresponding 2-amino-3-oxo-fatty acid methyl ester hydrochloride as the starting compound, there were obtained the following compounds (Examples 7 and 8).

EXAMPLE 7

(1) Methyl 2-cinnamoylamino-4-methyl-3-oxovalerate: Yield 79.3%, mp 74°–75° C. (recrystallized from isopropyl ether).

(2) 5-Isopropyl-2-styryl-4-oxazolecarboxylic acid: Yield 99.3%, mp 141°–142° C. (recrystallized from isopropyl ether).

(3) 4-Hydroxymethyl-5-isopropyl-2-styryloxazole: Yield 84.7%, mp 91°–92° C. (recrystallized from ethyl ether).

(4) 5-Isopropyl-2-styryl-4-oxazoleacetic acid: Yield 65.3%, mp 155°–156° C. (recrystallized from ethanol).

EXAMPLE 8

(1) Methyl 2-cinnamoylamino-3-oxononanoate: Yield 90.3%, mp 85°–86° C. (recrystallized from isopropyl ether).

(2) 5-Hexyl-2-styryl-4-oxazolecarboxylic acid: Yield 97.4%, mp 133°–134° C. (recrystallized from isopropyl ether).

(3) 5-Hexyl-4-hydroxymethyl-2-styryloxazole: Yield 63.2%, mp 44°–45° C. (recrystallized from hexane).

(4) 5-Hexyl-2-styryl-4-oxazoleacetic acid: Yield 70.3%, mp 107°–108° C. (recrystallized from isopropyl ether).

EXAMPLE 9

(1) A mixture of cyclopentanecarboxylic acid (9.2 g) and thionyl chloride (12 ml) was refluxed for 30 minutes and the thionyl chloride was distilled off. The thus-obtained cyclopentanecarbonyl chloride was dissolved in chloroform (150 ml), and ethyl 2-aminoacetoacetate hydrochloride (14.5 g) was added. Triethylamine (26.9 ml) was added dropwise with ice-cooling and stirring and the mixture was stirred for an hour, washed with water, 1N hydrochloric acid and water in that order and dried over anhydrous magnesium sulfate. The solvent was then distilled off and toluene (150 ml) and phosphorus oxychloride (22.3 ml) were added to the residue. The mixture was refluxed with stirring for 1.5 hours. The solvent was distilled off and the residue was neutralized with aqueous sodium hydrogen carbonate and extracted with ethyl ether. The ethyl ether layer was washed with water and dried over anhydrous magnesium sulfate. The solvent was distilled off and the oily residue was purified by chromatography using silica gel (200 g) [eluent: hexane-acetone (9:1)] to give ethyl 2-cyclopentyl-5-methyl-4-oxazolecarboxylate (11.3 g) as an oil. This product was dissolved in ethanol (50 ml), and 2N sodium hydroxide (50 ml) was added. The mixture was heated on a water bath at 90° C. for 5 minutes, diluted with water and adjusted to pH 2 with hydrochloric acid to give 2-cyclopentyl-5-methyl-4-oxazolecarboxylic acid as crystals; yield 8.2 g (52.9%). Recrystallization from isopropyl ether gave colorless prisms melting at 119°–120° C.

Elemental analysis; Calcd. for $C_{10}H_{13}NO_3$: C, 61.53; H, 6.71; N, 7.17; Found: C, 61.43; H, 6.72; N, 7.13.

(2) A mixture of 2-cyclopentyl-5-methyl-4-oxazolecarboxylic acid (7.0 g) and thionyl chloride (14 ml) was refluxed with stirring for 40 minutes. The thionyl chloride was completely distilled off and the residue was dissolved in dimethoxyethane (70 ml). The solution was added dropwise to a mixture of sodium borohydride (2.7 g) and dimethoxyethane (50 ml) with ice-cooling and stirring. The mixture was stirred for 30 minutes, adjusted to pH 2 with 2N hydrochloric acid and refluxed for 30 minutes. The solvent was then distilled off and aqueous sodium hydrogen carbonate was added. The mixture was extracted with ethyl ether and the ethyl ether layer was washed with water and dried over anhydrous magnesium sulfate. The solvent was distilled off and the residue was purified by chromatography using silica gel (75 g) [eluent: hexane-acetone (7:3)] to give 2-cyclopentyl-4-hydoxymethyl-5-methyloxazole as an oil; yield 4.0 g (61.5%).

NMR (CDCl$_3$) δ: 1.72 (8H, broad), 2.23 (3H, s), 3.13 (1H, borad), 4.37 (2H, s), 4.88 (1H, broad s).

(3) Thionyl chloride (8 ml) was added dropwise to 2-cyclopentyl-4-hydroxymethyl-5-methyloxazole (4.0 g) with ice-cooling and stirring and the mixture was further stirred for 10 minutes. The thionyl chloride was distilled off and aqueous sodium hydrogen carbonate was added to the residue. The mixture was extracted with ethyl ether and the ethyl ether layer was washed with water and dried over anhydrous magnesium sulfate. The solvent was then distilled off and the residue was dissolved in dimethyl sulfoxide (40 ml), followed by addition of sodium cyanide (1.3 g). The mixture was stirred for 5 hours, diluted with water and extracted with ethyl ether. The ethyl ether layer was washed with water and dried over anhydrous magnesium sulfate. The solvent was distilled off and ethanol (20 ml) and 2N sodium hydroxide (20 ml) were added to the residue. The mixture was refluxed with stirring for 3.5 hours diluted with water and washed with ethyl ether. The aqueous layer was adjusted to pH 2 with hydrochloric acid and extracted with ethyl ether. The ethyl ether extract was washed with water and dried over anhydrous magnesium sulfate. The solvent was distilled off and the residue was treated with isopropyl ether to give 2-cyclopentyl-5-methyl-4-oxazoleacetic acid as crystals; yield 1.56 g (33.8%). Recrystallization from isopropyl ether gave colorless needles melting at 83°–84° C.

Elemental analysis; Calcd. for $C_{11}H_{15}NO_3$: C, 63.14; H, 7.23; N, 6.69; Found: C, 63.14; H, 7.13; N, 6.73.

Following the procedure of Example 9 and using the corresponding acid chloride, the following compounds (Examples 10–12) were obtained.

EXAMPLE 10

(1) 2-Cyclohexyl-5-methyl-4-oxazolecarboxylic acid: Yield 40.7%, mp 173°–174° C. (recrystallized from ethanol-water).

(2) 2-Cyclohexyl-4-hydroxymethyl-5-methyloxazole: Yield 71.4%, an oil.

(3) 2-Cyclohexyl-5-methyl-4-oxazoleacetic acid: Yield 49.8%, mp 102°–103° C. (recrystallized from isopropyl ether).

Elemental analysis; Calcd. for $C_{12}H_{17}NO_3$: C, 64.55; H, 7.67; N, 6.27; Found: C, 64.68; H, 7.49; N, 6.47.

EXAMPLE 11

(1) 5-Methyl-2-(1-methylcyclohexyl)-4-oxazolecarboxylic acid: Yield 68.0%, mp 128°–129° C. (recrystallized from isopropyl ether).

(2) 4-Hydroxymethyl-5-methyl-2-(1-methylcyclohexyl)oxazole: Yield 84.5%, oil.

(3) 4-Cyanomethyl-5-methyl-2-(1-methylcyclohexyl)oxazole: Yield 87.2%, mp 57°–58° C. (recrystallized from isopropyl ether).

(4) 5-Methyl-2-(1-methylcyclohexyl)-4-oxazoleacetic acid: Yield 76.5%, mp 67°–68° C. (recrystallized from hexane).

Elemental analysis; Calcd. for $C_{13}H_{19}NO_3$: C, 65.80; H, 8.07; N, 5.90; Found: C, 65.86; H, 7.85; N, 5.86.

EXAMPLE 12

(1) 5-Methyl-2-(1-methyl-3-cyclohexen-1-yl)-4-oxazolecarboxylic acid: Yield 63.8%, oil.

(2) 4-Hydroxymethyl-5-methyl-2-(1-methyl-3-cyclohexen-1-yl)oxazole: Yield 53.1%, oil.

(3) 5-Methyl-2-(1-methyl-3-cyclohexen-1-yl)-4-oxazoleacetic acid: Yield 67.2%, mp 144°–145° C. (recrystallized from ethanol).

EXAMPLE 13

(1) Ethyl chlorocarbonate (2.0 ml) was added dropwise to a mixture of cinnamic acid (2.96 g), dichloromethane (60 ml) and triethylamine (2.8 ml) under cooling with ice-sodium chloride and stirring, and the whole mixture was stirred for 10 minutes. L-Aspartic acid β-methyl ester hydrochloride (3.67 g) was added and triethylamine (5.6 ml) was further added dropwise. The resulting mixture was stirred at room temperature for 40 minutes, washed with 2N hydrochloric acid and water and dried over anhydrous magnesium sulfate. The solvent was then distilled off. To the thus-obtained N-cynnamoyl-L-aspartic acid β-methyl ester were added acetic anhydride (15 ml), triethylamine (15 ml) and 4-dimethylaminopyridine (0.2 g) and the mixture was stirred for 30 minutes, poured into water, stirred for 10 minutes for decomposition and extracted with ethyl acetate. The ethyl acetate layer was washed with diluted hydrochloric acid, water, aqueous sodium hydrogen carbonate and water, and dried over anhydrous magnesium sulfate. The solvent was distilled off and the residue was treated with isopropyl ether to give methyl 3-cinnamoylamino- 4-oxovalerate as crystals; yield 2.65 g (48.1%). Recrystallization from ethyl ether gave colorless needles melting at 82°–83° C.

Elemental analysis; Calcd. for $C_{15}H_{17}NO_4$: C, 65.44; H, 6.88; N, 5.09; Found: C, 65.58; H, 6.25; N, 4.98.

(2) A mixture of methyl 3-cinnamoylamino-4-oxovalerate (2.2 g), phosphorus oxychloride (2.2 ml) and toluene (24 ml) was refluxed with stirring for an hour. The solvent was distilled off and the residue was neutralized with aqueous sodium hydrogen carbonate and extracted with ethyl ether. The ethyl ether layer was washed with water and dried over anhydrous magnesium sulfate. The solvent was then distilled off and ethanol (8 ml) and 2N sodium hydroxide (8 ml) were added to the residue. The mixture was stirred for 30 minutes and adjusted to pH 2 with diluted hydrochloric acid. The resulting crystalline precipitate was collected by filtration to give 5-methyl-2-styryl-4-oxazoleacetic acid; yield 1.50 g (77.3%). Recrystallization from ethanol gave pale brown needles melting at 182°–183° C. The IR and NMR spectra of this product were in good agreement with those of the compound obtained in Example 1.

EXAMPLE 14

Proceeding in the same manner as Example 13 but using cyclohexanecarboxylic acid in lieu of cinnamic acid, there were obtained the following compounds:

(1) N-Cyclohexylcarbonyl-L-aspartic acid β-methyl ester: Yield 68.5%, mp 79°–81° C. (recrystallized from ethyl ether).

(2) Methyl 3-cyclohexylcarbonylamino-4-oxovalerate: Yield 65.1%, mp 87°–88° C. (recrystallized from isopropyl ether).

(3) 2-Cyclohexyl-5-methyl-4-oxazoleacetic acid: Yield 69.3%, mp 104°–105° C. (recrystallized from isopropyl ether). The IR and NMR spectra of this product were in good agreement with those of the compound obtained in Example 10.

EXAMPLE 15

(1) Triethylamine (100.8 ml) was added to a mixture of L-aspartic acid β-methyl ester hydrochloride (36.7 g) and dichloromethane (370 ml) under cooling with ice-sodium chloride and stirring, followed by dropwise addition of 1-methylcyclohexylcarbonyl chloride (32.0 g). The resulting mixture was stirred with cooling for an hour, washed with diluted hydrochloric acid and water and dried over anhydrous magnesium sulfate. The solvent was distilled off and the residue was treated with hexane to give N-(1-methylcyclohexylcarbonyl)-L-aspartic acid β-methyl ester as crystals; yield 48.0 g (88.4%). An aliquot of the crystals were recrystallized from isopropyl ether to give colorless prisms melting at 88°–89° C.

Elemental analysis; Calcd. for $C_{13}H_{21}NO_5$: C, 57.55; H, 7.80; N, 5.16; Found: C, 57.63; H, 7.72; N, 5.41.

(2) A mixture of N-(1-methylcyclohexylcarbonyl)-L-aspartic acid β-methyl ester (48.0 g), acetic anhydride (106 ml), pyridine (88 ml) and 4-dimethylaminopyridien (1.06 g) was heated with stirring on an ice bath at 90° C. for 2 hours. Water (100 ml) was added dropwise at the same temperature and the mixture was further stirred for 15 minutes. After cooling, the reaction mixture was diluted with water and extracted with ethyl acetate. The ethyl acetate layer was washed with water, diluted hydrochloric acid, water, aqueous sodium hydrogen carbonate and water in that order, and dried over anhydrous magnesium sulfate. The solvent was then distilled off and the residue was treated with isopropyl ether to give methyl 3-(1-methylcyclohexylcarbonylamino)-4-oxovalerate as crystals; yield 45.0 g (94.5%). An aliquot of the crystals was recrystallized from isopropyl ether to give colorless needles melting at 54°–55° C.

Elemental analysis; Calcd. for $C_{14}H_{23}NO_4$: C, 62.43; H, 8.61; N, 5.20; Found: C, 62.63; H, 8.33; N, 5.35.

(3) A mixture of methyl 3-(1-methylcyclohexylcarbonylamino)-4-oxovalerate (45.0 g), toluene (250 ml) and phosphorus oxychloride (50 ml) was refluxed with stirring for 5 hours. The solvent and the phosphorus oxychloride were distilled off and water was added to the residue. The mixture was neutralized with potassium carbonate and extracted with ethyl ether. The ethyl ether layer was washed with water and dried over anhydrous magnesium sulfate. The solvent was distilled off and the residue was further distilled under reduced pressure to give methyl 5-methyl-2-(1-methylcyclohexyl)-4-oxazcleacetic acid as an oil; yield 30.5 g (72.6%). bp 110°–113° C. (0.2 mmHg)

NMR (CDCl$_3$) δ: 1.22 (3H, s), 1.42 (8H, broad), 2.12 (2H, broad), 2.22 (3H, s), 3.45 (2H, s), 3.65 (3H, s).

(4) To a solution of methyl 5-methyl-2-(1-methylcyclohexyl)-4-oxazoleacetate (64.3 g) in ethanol (100 ml) was added 2N sodium hydroxide (170 ml). The mixture was stirred at room temperature for 30 minutes, diluted with water, adjusted to pH 2 with hydrochloric acid and extracted with ethyl ether. The ethyl ether layer was washed with water and dried over anhydrous magnesium sulfate. The magnesium sulfate was filtered off and morpholine (23 ml) was added. The resulting crystalline precipitate was collected by filtration to give 5-methyl-2-(1-methylcyclohexyl)-4-oxazoleacetic acid morpholine salt, yield 75.0 g. Recrystallization from acetone gave colorless needles melting at 109°–110° C. Yield 66.0 g.

The above crystals were dissolved in water (200 ml) and the solution was adjusted to pH 2 by addition of 6N hydrochloric acid with ice-cooling and vigorous stirring. The reaction mixture was further stirred for a while to give 5-methyl-2-(1-methylcyclohexyl)-4oxazoleacetic acid as crystals; yield 44.9 g (74.0%). Recrystallization from hexane gave colorless prisms melting at 67°–68° C. Yield 43.0 g (70.8%). The IR and NMR spectra were in good agreement with those of the compound obtained in Example 11.

EXAMPLE 16

(1) 1-Methylcyclohexylcarbonyl chloride (1.6 g) was added dropwise to a mixture of L-aspartic acid β-benzyl ester (2.23 g), dichloromethane (30 ml) and triethylamine (30 ml) with ice-cooling and stirring. The resulting mixture was stirred with ice-cooling for an hour, washed with 1N hydrochloric acid and water and dried over anhydrous magnesium sulfate. The solvent was then distilled off and the oily residue (3.2 g) was dissolved in dimethoxyethane (30 ml). Acetic anhydride (4 ml), pyridine (4.8 ml) and 4-dimethylaminopyridine (0.12 g) were added and the mixture was refluxed for 1.5 hours. Acetic acid (2 ml) was added and the whole mixture was refluxed for 2.5 hours. The solvent was distilled off and water was added. The mixture was extracted with ethyl acetate and the ethyl acetate layer was washed with diluted hydrochloric acid, water, aqueous sodium hydrogen carbonate and water in that order, and dried over anhydrous magnesium sulfate. The residue (2.0 g) was purified by chromatography on silica gel (40 g) [eluent: hexane-acetone (9:1)] to give benzyl 3-(1-methylcyclohexylcarbonylamino)-4-oxovalerate as an oil; yield 1.2 g (34.8%).

NMR (CDCl$_3$) δ: 1.13 (3H, s), 1.38 (8H, broad), 1.90 (2H, broad), 2.22 (3H, s), 2.90 (2H, m), 4.72 (1H, m), 5.07 (2H, s), 6.83 (1H, d), 7.28 (5H, s).

(2) A mixture of benzyl 3-(1-methylcyclohexylcarbonylamino)-4-oxovalerate (1.2 g), toluene (20 ml) and phosphorus oxychloride (2.0 ml) was refluxed with stirring for 4 hours. The solvent was distilled off and aqueous sodium hydrogen carbonate was added. The mixture was extracted with ethyl ether and the ethyl ether layer was washed with water and dried over anhydrous magnesium sulfate. The solvent was then distilled off and the residue was purified by chromatography on silica gel (13 g) [eluent: hexaneacetone (9:1)] to give benzyl 5-methyl-2-(1-methylcyclohexyl)- 4-oxazoleacetate; yield 1.0 g (87.7%).

NMR (CDC1$_3$) δ: 1.23 (3H, s), 1.43 (8H, b), 2.10 (2H, b), 2.20 (3H, s). 3.50 (2H, s), 5.10 (2H, s), 7.23 (5H, s).

(3) Benzyl 5-methyl-2-(1-methylcyclohexyl)-4-oxazoleacetate (1.0 g) was dissolved in ethanol (3 ml), and 2N sodium hydroxide (3 ml) was added. The mixture was heated on a water bath at 90° C. for 5 minutes, diluted with water and washed with ethyl ether. The aqueous layer was adjusted to pH 2 with hydrochloric acid and extracted with ethyl ether. The ethyl ether extract was washed with water and dried over anhydrous magnesium sulfate. The solvent was distilled off and the residue was recrystallized from hexane to give 5-methyl-2-(1-methylcyclohexyl)-4-oxazoleacetic acid as crystals; yield 0.41 g (56.9%). Mp 66°–67° C. The IR and NMR spectra of this product were in good agreement with those of the compound obtained in Example 15.

EXAMPLE 17

(1) A mixture of 1-methyl-3-cyclohexenecarboxylic acid (2.8 g) and thionyl chloride (5 ml) was refluxed with stirring for an hour and the thionyl chloride was distilled off to give as an oil 1-methyl-3-cycylohexen-1-ylcarbonyl chloride. This oil was dissolved in dichloromethane (10 ml) and the solution was added dropwise to a mixture of L-aspartic acid β-methyl ester hydrochloride (3.67 g), dichloromethane (50 ml) and triethylamine (10 ml) under cooling with ice-sodium chloride. The resulting mixture was stirred with cooling for an hour, washed with 1N hydrochloric acid and water and dried over anhydrous magnesium sulfate. The solvent was distilled off to give N-(1-methyl-3-cyclohexen-1-ylcarbonyl)-L-aspartic acid β-methyl ester as an oil; yield 5.2 g (96.3%).

NMR (CDCl$_3$) δ: 1.20 (3H, s), 1.4–2.5 (6H, m), 3.0 (2H, m), 3.63 (3H, s), 4.8–5.0 (1H, m), 5.6 (2H, broad s), 6.9 (1H, d, J=8), 11.28 (1H, s).

(2) A mixture of N-(1-methyl-3-cyclohexen-1 ylcarbonyl)-L-aspartic acid 8-methyl ester (5.1 g), acetic anhydride (20 ml), triethylamine (20 ml) and 4-dimethylaminopyridine (0.3 g) was stirred at room temperature for 30 minutes and at 90° C. for an hour and poured into water (150 ml). The whole mixture was stirred for 30 minutes and extracted with ethyl acetate. The ethyl acetate layer was washed with water and dried over anhydrous magnesium sulfate. The solvent was then distilled off and the residue was purified by chromatography on silica gel (80 g) [eluent: benzeneacetone (10:1)]to give 3-(1-methyl-3-cyclohexen-1-yl-carbonylamino)-4-oxovalerate as an oil; yield 3.9 g (76.5%).

NMR (CDCl$_3$) δ: 1.26 (3H, s), 1.5–2.5 (6H, m), 2.18 (3H, s), 2.8–3.0 (2H, m), 3.66 (3H, s), 4.5–4.9 (1H, m), 5.63 (2H, broad s), 6.93 (1H, d, J=8).

(3) A mixture of methyl 3-(1-methyl-3-cyclohexen-1-ylcarbonylamino)-4-oxovalerate (3.4 g), toluene (50 ml) and phosphorus oxychloride (3.5 ml) was refluxed for 3 hours and the solvent was distilled off. Aqueous sodium hydrogen carbonate was added, followed by extraction with ethyl acetate. The ethyl acetate layer was washed with water and dried over anhydrous magnesium sulfate. The solvent was distilled off and the oily residue was further distilled under reduced pressure to give methyl 5-methyl-2-(1-methyl-3-cyclohexen-1-yl)-4-oxazoleacetate as an oil; yield 2.5 g (78.1%). Bp 120°–123° C. (0.3 mmHg).

NMR (CDCl$_3$)δ: 1.29 (3H, s), 1.5–2.5 (6H, m), 2.22 (3H, s), 3.43 (2H, s), 3.65 (3H, s), 5.62 (2H, broad s).

(4) To a solution of methyl 5-methyl-2-(1-methyl-S 3-cyclohexen 1-yl)-4-oxazoleacetate (4.8 g) in ethanol (15 ml) was added 2N potassium hydroxide (15 ml). The mixture was stirred for 30 minutes, acidified with hydrochloric acid, diluted with water and extracted with ethyl acetate. The ethyl acetate layer was washed with water and dried over anhydrous magnesium sulfate. The solvent was then distilled off to give 5-methyl-2-(1-methyl-3-cyclohexen-1-yl)-4-oxazoleacetic acid as crystals; yield 3.75 g (82.6%). Recrystallization from ethanol gave colorless prisms melting at 144–145° C. The IR and NMR spectra of this product were in good agreement with those of the compound obtained in Example 12.

EXAMPLE 18

(1) Ethyl chlorocarbonate (3.0 ml) was added dropwise to a mixture of cycloheptanecarboxylic acid (4.26 g), dichloromethane (90 ml) and triethylamine (4.2 ml) under cooling with ice-sodium chloride and stirring. The resulting mixture was stirred for 10 minutes and L-aspartic acid 8-methyl ester hydrochloride (5.5 g) was added, followed by dropwise addition of triethylamine (8.4 ml). The whole mixture was stirred with cooling for 30 minutes and at room temperature for 30 minutes, then washed with diluted hydrochloric acid and dried over anhydrous magnesium sulfate. The solvent was then distilled off and acetic anhydride (24 ml), triethylamine (24 ml) and 4-dimethylaminopyridine (0:36 g) were added to the residue. The mixture was stirred for 4 hours, diluted with water, stirred for 20 minutes and extracted with ethyl acetate. The ethyl acetate layer was washed with water, aqueous sodium hydrogen carbonate and water in that order, and dried over anhydrous magnesium sulfate. The solvent was distilled off and the residue was treated with isopropyl ether to give methyl 3-cycloheptylcarbonylamino-4-oxovalerate as crystals; yield 6.1 g (75.6%). An aliquot of the crystals was recrystallized from isopropyl ether to give colorless needles melting at 64°–65° C.

Elemental analysis; Calcd. for C$_{14}$H$_{23}$NO$_4$: C, 62.43; H, 8.61; N, 5.20; Found: C, 62.59; H, 8.63; N, 5.17. (2) A mixture of methyl 3-cycloheptylcarbonyl-amino-4-oxovalerate (7.0 g), toluene (70 ml) and phosphorus oxychloride (7.3 ml) was refluxed with stirring for 2.5 hours. The solvent was then distilled off and aqueous sodium hydrogen carbonate was added. The mixture was extracted with ethyl acetate and the ethyl acetate layer was washed with water and dried over anhydrous sodium sulfate. The solvent was distilled off and the residue was dissolved in ethanol (50 ml), followed by addition of 2N sodium hydroxide (26 ml). The mixture was allowed to stand at room temperature for 30 minutes, diluted with water, adjusted to pH 2 with hydrochloric acid and extracted with ethyl acetate. The ethyl acetate layer was washed with water and dried over anhydrous magnesium sulfate. The solvent was distilled off and the residue was treated with hexane to give 2-cycloheptyl-5-methyl-4-oxazoleacetic acid as crystals; yield 5.0 g (81.0%). Recrystallization from isopropyl ether gave colorless needles melting at 84°–85° C.

Elemental analysis; Calcd. for C$_{13}$H$_{19}$NO$_3$: C, 65.80; H, 8.07; N, 5.90; Found: C, 66.03; H, 8.17; N, 5.90.

EXAMPLE 19

(1) A mixture of N-cyclohexylcarbonyl-L-aspartic acid β-methyl ester (5.14 g) as obtained in Example 14-(1), propionic anhydride (16 ml), triethylamine (16 ml) and 4-dimethylaminopyridine (0.24 ml) was stirred at room temperature for an hour, diluted with water, stirred for 30 minutes, and extracted with ethyl acetate. The ethyl acetate layer was washed with water, aqueous sodium hydrogen carbonate and water in that order and dried over anhydrous magnesium sulfate. The solvent was then distilled off and the crystalline residue was collected by filtration and washed with hexane to give methyl 3-cyclohexylcarbonyl-amino-4-oxohexanoate; yield 3.1 g (57.6%). Recrystallization from isopropyl ether gave colorless needles melting at 99°–100° C.

Elemental analysis; Calcd. for C$_{14}$H$_{23}$NO$_4$: C, 62.43; H, 8.61; N, 5.20; Found: C, 62.97; H, 9.06; N, 4.98.

(2) Proceeding in the same manner as Example 18-(2) and using methyl 3-cyclohexylcarbonylamino-4oxohexanoate (2.69 g), there was obtained 2-cyclohexyl- 5-ethyl-4-oxazoleacetic acid. Yield 2.2 g (92.8%). Recrystallization from hexane gave colorless plates melting at 101°–102° C.

Elemental analysis; Calcd. for C$_{13}$H$_{19}$NO$_3$: C, 65.80; H, 8.07; N, 5.90; Found: C, 65.90; H, 8.01; N, 5.76.

EXAMPLE 20

(1) A mixture of N-cyclohexylcarbonyl-L-aspartic acid β-methyl ester (4.1 g) as obtained in Example 14(1), butyric anhydride (13 ml), triethylamine (13 ml) and 4-dimethylaminopyridine (0.2 g) was treated in the same manner as Example 19-(1) to give methyl 3-cyclohexylcarbonylaminio-4-oxoheptanoate as crystals; yield 2.4 g (53.2%). Recrystallization from isopropyl ether gave colorless needles melting at 82°–83° C.

Elemental analysis; Calcd. for C$_{15}$H$_{25}$NO$_4$: C, 63.58; H, 8.89; N, 4.94; Found: C, 64.35; H, 9.29; N, 4.78.

(2) Proceeding in the same manner as Example 18-(2) and using methyl 3-cyclohexylcarbonylamino-4oxoheptanoate (2.35 g), there was obtained 2-cyclohexyl-5-propyl-4-oxazoleacetic acid. Yield 2.0 g (96.2%). Recrystallization from hexane gave colorless needles melting at 110°–111° C.

Elemental analysis; Calcd. for C$_{14}$H$_{21}$NO$_{03}$: C, 66.91; H, 8.42; N, 5.57; Found: C, 67.07; H, 8.35; N, 5.59.

EXAMPLE 21

In the same manner as Example 18, there were obtained the following compounds:
(1) Methyl 3-cyclohexylacetylamino-4-oxovalerate: Yield 63.7%, mp 75°–76° C. (recrystallized from isopropyl ether).

(2) 2-Cycylohexylmethyl-5-methyl-4-oxazoleacetic acid: Yield 88.7%, mp 104°-105° C. (recrystallized from ethyl ether).

Elemental analysis; Calcd. for $C_{13}H_{19}NO_3$: C, 65.80; H, 8.07; N, 5.90; Found: C, 65.92; H, 8.03; N, 6.00.

EXAMPLE 22

In the same manner as Example 18, there were obtained the following compounds:

(1) Methyl 3-(3-cyclohexen-1-ylcarbonylamino)-4-oxovalerate: Yield 64.4%, mp 69-70° C (recrystallized from ethyl ether).

(2) 2-(3-Cyclohexen-1-yl)-5-methyl-4-oxazoleacetic acid: Yield 48.6%, mp 86°-87° C. (recrystallized from isopropyl ether).

Elemental analysis; Calcd. for $C_{12}H_{15}NO_3$: C, 65.14; H, 6.83; N, 6.33; Found: C, 64.96; H, 6.50; N, 6.08.

EXAMPLE 23

In the same manner as Example 18, there were obtained the following compounds:

(1) Methyl 3-(2,2-dimethylvaleroylamino)-4oxovalerate: Yield 49.3%, an oil (purified by silica gel chromatography).

(2) 5-Methyl-2-(1,1-dimethylbutyl)-4-oxazoleacetic acid: Yield 51.0%, mp 97°-98° C. (recrystallized from isopropyl ether).

Elemental analysis; Calcd. for $C_{12}H_{19}NO_3$: C, 63.98; H, 8.50; N, 6.22; Found: C, 63.89; H, 8.50; N, 6.36.

EXAMPLE 24

(1) A mixture of endo-5-norbornene-2-carboxylic acid (6.9 g) and thionyl chloride (7.2 ml) was refluxed for 20 minutes. The thionyl chloride was distilled off, the residue was dissolved in dichloromethane (10 ml) and the solution was added dropwise to a mixture of L-aspartic acid β-methyl ester hydrochloride (9.2 g), dichloromethahe (150 ml) and triethylamine (25.2 ml) with ice-cooling and stirring. The resulting mixture was stirred for an hour, washed with 2N hydrochloric acid and water and dried over anhydrous magnesium sulfate. The solvent was then distilled off and the residue was dissolved in a mixture of acetic anhydride (40 ml) and triethylamine (40 ml). 4-Dimethylaminopyridine (0.6 g) was added and the mixture was stirred at room temperature for 30 minutes and on water bath at 80°-90° C. for 30 minutes, poured into water (100 ml), stirred for 30 minutes, and extracted with ethyl acetate. The ethyl acetate layer was washed with water, sodium hydrogen carbonate and water in that order and dried over anhydrous magnesium sulfate. The solvent was distilled off and the residue was purified by chromatography on silica gel (120 g) [eluent: hexane-acetone (7:3)]to give methyl 3-(endo-5-norbornen-2-yl)carbonylamino4-oxovalerate as an oil; yield 8.0 g (60,6%).

(2) A mixture of methyl 3-(endo-5-norbornen-2-yl)carbonylamino-4-oxovalerate (8.0 g), toluene (80 ml, and phosphorus oxychloride (8.4 ml) was stirred for 3.5 hours. The solvent was distilled off, and the residue was neutralized with aqueous sodium hydrogen carbonate and extracted with ethyl acetate. The ethyl acetate layer was washed with water and dried over anhydrous magnesium sulfate. The solvent was then distilled off and the residue was purified by silica gel chromatography [eluent: hexane-ethyl ether (1:1)]to give methyl 5-methyl-2-(endo-5-norbornen-2-yl)-4oxazoleacetate as an oil; yield 3.6 g.

NMR (CDCl$_3$) δ: 1.43 (4H, m), 2.10 (1H, m), 2.18 (3H, s), 2.92 (1H, broad), 3.27 (1H, b), 3.38 (2H, s), 3.65 (3H, s), 5.83 (1H, q), 6.13 (1H, q).

The above oil was dissolved in ethanol (15 ml), and 2N sodium hydroxide (15 ml) was added. The mixture was allowed to stand at room temperature for 20 minutes, then adjusted to pH 2 with hydrochloric acid, diluted with water and extracted with ethyl ether. The ethyl ether layer was washed with water and dried over anhydrous magnesium sulfate. The solvent was distilled off to give 5-methyl-2-(endo-5-ncrbornen-2-yl)-4-oxazcleacetic acid as crystals:yield 2.5 g (35.7%). Recrystallization from isopropyl ether gave colorless needles melting at 112°-113° C.

Elemental analysis; Calcd. for $C_{13}H_{15}NO_3$: C, 66.94; H, 6.48; N, 6.00; Found: C, 66.89; H, 6.47; N, 5.82.

EXAMPLE 25

To a solution of 5-methyl-2-(endo-5-norbornen-2-yl)-4-oxazoleacetic acid (1.0 g) in ethyl acetate(15 ml) was added 10% palladium-on-carbon (50% wet, 0.2 g) and the mixture was hydrogenated at ordinary pressure. The catalyst was filtered off and the filtrate was concentrated. The residue was recrystallized from isopropyl ether to give 5-methyl-2-(endo-2-norbornyl)4-oxazoleacetic acid as colorless needles; yield 0.75 g. mp 108°-109° C.

Elemental analysis; Calcd. fcr $C_{13}H_{17}NO_3$: C, 66.36; H, 7.28; N, 5.95; Found: C, 65.97; H, 7.06; N, 5.64.

EXAMPLE 26

(1) In the same manner as Example 24-(1), L-aspartic acid β-methyl ester was reacted with pivaloyl chloride followed by reaction treatment in a mixture of acetic anhydride, triethylamine and 4-dimethylaminopyridine to give methyl 4-oxo-3-pivaloylaminovalerate as crystals. Yield 27.5%. Mp 68°-69° C. (recrystallized from isopropyl ether).

(2) Methyl 4-oxo-3-pivaloylaminovalerate was dissolved in acetic anhydride (15 ml), and concentrated sulfuric acid (1.2 ml) was added dropwise with stirring. The mixture was allowed to stand at room temperature for 20 minutes and heated at 80° C. for 5 minutes. The acetic anhydride was distilled off under reduced pressure and the residue was poured into 50 ml of ice water. The mixture was neutralized with potassium carbonate and extracted with ethyl ether. The ethyl ether layer was washed with water and dried over anhydrous magnesium sulfate. The solvent was then distilled off and the oily residue (2.5 g) was stirred in a mixture of ethanol (13 ml) and 2N sodium hydroxide (13 ml) at room temperature for 30 minutes. The reaction mixture was diluted with water, adjusted to pH 2 with hydrochloric acid and extracted with ethyl ether. The ethyl ether layer was washed with water and dried over anhydrous magnesium sulfate. The solvent was distilled off and the residue was treated with hexane to give 2-tert-butyl-5-methyl-4-oxazoleacetic acid as crystals; yield 1.50 g (60.2%). Recrystallization from isopropyl ether gave colorless prisms melting at 121°-122° C.

Elemental analysis; Calcd. for $C_{10}H_{15}NO_3$: C, 60.90; H, 7.67; N, 7.10; Found: C, 60.72; H, 7.71; N, 7.12.

FORMULATION EXAMPLE

For use as therapeutic agents for diabetes, the compound (I) of the present invention can be used in the following exemplary formulations.

| A. Tablets | |
| --- | --- |
| (1) 2-(1-Methylcyclohexyl)-5-methyl-4-oxazoleacetic acid | 30 g |
| (2) Lactose | 70 g |
| (3) Corn starch | 29 g |
| (4) Magnesium stearate | 1 g |
| | 130 g for 1000 tablets |

The whole amounts of (1) and (2) and 17 g of corn starch were blended and combined with a paste prepared from 7 g of corn starch. The mixture was granulated and 5 g of corn starch and the indicated amount of (4) were further added. This composition was molded on a compression tablet machine to give 1000 tablets 7 mm in diameter and each containing 30 mg of (1).

| B. Capsules | |
| --- | --- |
| (1) 2-Cyclohexyl-5-methyl-4-oxazoleacetic acid | 30 g |
| (2) Lactose | 115 g |
| (3) Microcrystalline cellulose | 70 g |
| (4) Magnesium stearate | 5 g |
| | 220 g for 1000 capsules |

The whole ingredients were mixed and filled into 1000 No. 3 gelatin capsules (Japanese Pharmacopeia, 10th Edition) to give capsules each containing 30 mg of (1).

We claim:

1. A compound of the formula:

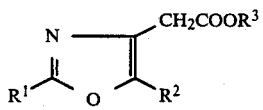

wherein $R^1$ is (A) a group of the formula,

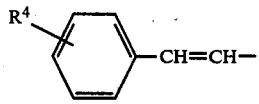

where $R^4$ is hydrogen, a halogen or trifluoromethyl group, or (B) a group of the formula,

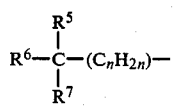

where n is 0 or an integer of 1 to 3; $R^5$ is hydrogen, or a straight chain or branched alkyl group of 1 to 6 carbon atoms; $R^6$ and $R^7$ are respectively a straight chain or branched alkyl group of 1 to 6 carbon atoms, a straight chain or branched alkenyl group of 2 to 6 carbon atoms, a cycloalkyl group of 3 to 7 carbon atoms, or a cycloalkenyl group of 5 to 7 carbon atoms; $R^6$ and $R^7$ may be combined with the neighbouring carbon atom to represent a cycloalkyl group of 3 to 7 carbon atoms, a cycloalkenyl group of 5 to 7 carbon atoms, a bicycloalkyl group of 7 to 10 carbon atoms, or a bicycloalkenyl group of 7 to 10 carbon atoms; provided, however, that when n is 0 and $R^5$ is hydrogen, $R^6$ and $R^7$ can be combined only to form a cycloalkenyl group of 5 to 7 carbon atoms, a bicycloalkyl group of 7 to 10 carbon atoms, or a bicycloalkenyl group of 7 to 10 carbon atoms; $R^2$ is a straight chain or branched alkyl group of 1 to 6 carbon atoms; and $R^3$ is hydrogen, a straight chain or branched alkyl group of 1 to 6 carbon atoms, or an aralkyl group, or a pharmaceutically acceptable salt thereof.

2. A compound as claimed in claim 1, wherein the group of the formula,

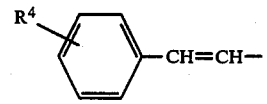

has trans-configuration.

3. A compound as claimed in claim 1, wherein $R^1$ is a group of the formula,

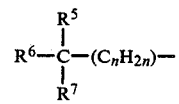

where $R^5$ is hydrogen, a straight chain or branched alkyl group of 1 to 3 carbon atoms, $R^6$ and $R^7$ are combined with the neightbouring carbon atoms to represent cycloalkyl group of 3 to 7 carbon atoms, or cycloalkenyl group of 3 to 7 carbon atoms, and n is 0 or 1, provided, however, that when n is zero and $R^5$ is hydrogen, $R^6$ and $R^7$ can be combined only to form a cycloalkenyl group of 3 to 7 carbon atoms.

4. A compound as claimed in claim 1, the compound of the formula being 5-methyl-2-styryl-4-oxazoleacetic acid, or a pharmaceutically acceptable salt thereof.

5. A compound as claimed in claim 1, the compound of the formula being 5-methyl-2-(1-methylcyclohexyl)-4-oxazoleacetic acid, or a methyl or benzyl ester or a pharmaceutically acceptable salt thereof.

6. A compound as claimed in claim 1, the compound of the formula being 5-methyl-2-(1-methyl-3-cyclohexen-1yl)-4-oxazoleacetic acid, or a pharmaceutically acceptable salt thereof.

7. A compound as claimed in claim 1, the compound of the formula being 2-cyclohexylmethyl-5-methyl-4-oxazoleacetic acid, or a pharmaceutically acceptable salt thereof.

8. A compound as claimed in claim 1, the compound of the formula being 2-(3-cyclohexen-1yl)-5-methyl-4-oxazoleacetic acid, or a pharmaceutically acceptable salt thereof.

9. A compound of the formula:

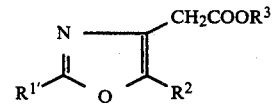

wherein $R^{1'}$ is a group of the formula:

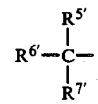

where $R^{5'}$ is hydrogen; $R^{6'}$ and $R^{7'}$ is combined with the neighbouring carbon atom to represent a cycloalkyl group of 3 to 7 carbon atoms; $R^2$ is a straight chain or branched alkyl group of 1 to 6 carbon atoms; and $R^3$ is hydrogen, a straight chain or branched alkyl group of 1 to 6 carbon atoms, or an aralkylgroup, or a pharmaceutically acceptable salt thereof.

10. A compound according to claim 9, which is 2-cyclopentyl-5-methyl-4-oxazoleacetic acid, or a pharmaceutically acceptable salt thereof.

11. A compound according to claim 9, which is 2-cyclohexyl-5-methyl-4-oxazoleacetic acid, or a pharmaceutically acceptable salt thereof.

12. A compound according to claim 9, which is 2-cycloheptyl-5-methyl-4-oxazoleacetic acid, or a pharmaceutically acceptable salt thereof.

13. A compound according to claim 9, which is 2-cyclohexyl-5-ethyl-4-oxazoleacetic acid, or a pharmaceutically acceptable salt thereof.

14. A compound according to claim 9, which is 2-cyclohexyl-5-propl-4-oxazoleacetic acid, or a pharmaceutically acceptable salt thereof.

15. A pharmaceutical composition comprising an antidiabetically effective amount of compound of the formula:

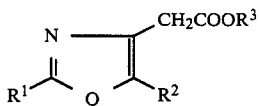

wherein $R^1$ is (A) a groupd of the formula,

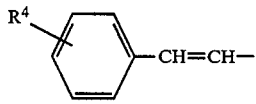

where $R^4$ is hydrogen, a halogen or trifluoromethyl group, or (B) a groupd of the formula,

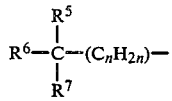

where n is 0 or an integer of 1 to 3; $R^5$ is hydrogen, or a straight chain or branched alkyl group of 1 to 6 carbon atoms; $R^6$ and $R^7$ are respectively a straight chain or branched alkyl group of 1 to 6 carbon atoms, a straight chain or branched alkenyl group of 2 to 6 carbon atoms, a cycloalkyl group of 3 to 7 carbon atoms, or a cycloalkenyl group of 5 to 7 carbon atoms; $R^6$ and $R^7$ may be combined with the neighbouring carbon atom to represent a cycloalkyl group of 3 to 7 carbon atoms, a cycloalkenyl group of 5 to 7 carbon atoms, a bicycloalkyl group of 7 to 10 carbon atoms, or a bicycloalkenyl group of 7 to 10 carbon atoms; provided, however, that when n is 0 and $R^5$ is hydrogen, $R^6$ and $R^7$ can be combined only to form a cycloalkenyl group of 5 to 7 carbon atoms, a bicycloalkyl group of 7 to 10 carbon atoms, or a bicycloalkenyl group of 7 to 10 carbon atoms; $R^2$ is a straight chain or branched alkyl group of 1 to 6 carbon atoms; and $R^3$ is hydrogen, a straight chain or branched alkyl group of 1 to 6 carbon atoms, or an aralkyl group, or a pharmaceutically acceptable salt thereof, and a pharmaceutically acceptable carrier, diluent or excipient thereof.

16. A method of treating diabetes by administering a thereapeutically effective amount of a compound of the formula:

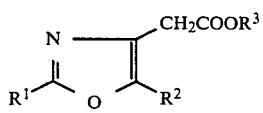

wherein $R^1$ is (A) a group of the formula,

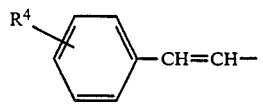

where $R^4$ is hydrogen, a halogen or trifluoromethyl group, or (B) a group of the formula,

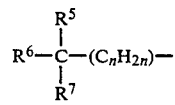

where n is 0 or an integer of 1 to 3; $R^5$ is hydrogen, or a straight chain or branched alkyl group of 1 to 6 carbon atoms; $R^6$ and $R^7$ are respectively a straight chain or branched alkyl group of 1 to 6 carbon atoms, a straight chain or branched alkenyl group of 2 to 6 carbon atoms, a cycloalkyl group of 3 to 7 carbon atoms, or a cycloalkenyl group of 5 to 7 carbon atoms; $R^6$ and $R^7$ may be combined with the neighbouring carbon atom to represent a cycloalkyl group of 3 to 7 carbon atoms, a cycloalkenyl group of 5 to 7 carbon atoms, a bicycloalkyl group of 7 to 10 carbon atoms, or a bicycloalkenyl group of 7 to 10 carbon atoms; $R^2$ is a straight chain or branched alkyl group of 1 to 6 carbon atoms; and $R^3$ is hydrogen, a straight chain or branched alkyl group of 1 to 6 carbon atoms, or an aralkyl group, or a pharmaceutically acceptable salt thereof.

* * * * *